US008104325B2

(12) United States Patent
Gerits et al.

(10) Patent No.: US 8,104,325 B2
(45) Date of Patent: Jan. 31, 2012

(54) DEVICE FOR COLLECTING GASES IN MOLTEN METAL AND MEASUREMENT METHOD

(75) Inventors: Erik Gerits, Genk (BE); Paul Clement Verstreken, Aarschot (BE); Jos Swennen, Meeuwen-Gruitrode (BE); Jozef Theodoor Aegten, Bocholt (BE)

(73) Assignee: Heraeus Electro-Nite International N.V., Houthalan (BE)

( * ) Notice: Subject to any disclaimer, the term of this patent is extended or adjusted under 35 U.S.C. 154(b) by 431 days.

(21) Appl. No.: 12/169,692

(22) Filed: Jul. 9, 2008

(65) Prior Publication Data
US 2009/0013757 A1    Jan. 15, 2009

(30) Foreign Application Priority Data
Jul. 10, 2007   (DE) .................. 10 2007 032 436

(51) Int. Cl.
G01N 33/20   (2006.01)
(52) U.S. Cl. .......................................... 73/19.07
(58) Field of Classification Search ............. 73/19.07
See application file for complete search history.

(56) References Cited

U.S. PATENT DOCUMENTS

| | | | |
|---|---|---|---|
| 2,861,450 A | 11/1958 | Ransley et al. | |
| 3,820,380 A * | 6/1974 | Miller et al. | 436/75 |
| 4,757,707 A * | 7/1988 | Harvey et al. | 73/19.07 |
| 5,518,931 A | 5/1996 | Plessers | |
| 6,216,526 B1 | 4/2001 | Junker et al. | |
| 7,685,863 B2 * | 3/2010 | Gerits et al. | 73/19.07 |
| 2007/0240488 A1 * | 10/2007 | Kreuser et al. | 73/19.07 |

FOREIGN PATENT DOCUMENTS

| | | |
|---|---|---|
| DE | 1084941 | 7/1960 |
| DE | 2423783 A1 | 12/1975 |
| DE | 3874423 T2 | 2/1993 |
| DE | 102005011181 A1 | 9/2006 |
| EP | 0295798 A1 | 5/1988 |
| EP | 0307430 B1 | 1/1992 |
| EP | 0563447 A1 | 11/1992 |
| WO | 8807197 A1 | 9/1988 |
| WO | 2006094668 A1 | 9/2006 |
| WO | WO 2006094668 A1 * | 9/2006 |

OTHER PUBLICATIONS

English Language Machine Translation of WO 20060946681. Publication date of WO 20060946681 is Sep. 2006. Translation obtained on Aug. 26, 2010.*
Office Action dated Jun. 23, 2009 for U.S. Appl. No. 11/908,007.

(Continued)

*Primary Examiner* — Lisa Caputo
*Assistant Examiner* — Punam Roy
(74) *Attorney, Agent, or Firm* — Panitch Schwarze Belisario & Nadel LLP

(57) ABSTRACT

A device is provided for collection of gases in molten metals, the device having an immersion end with a gas collection body, a gas supply line opening at the immersion end, and a gas discharge line for gases penetrating the gas collection body. The gas collection body has an end face arranged on the immersion end and side walls of the collection body, and at least one part of the gas collection body has a gas impermeable layer. A measurement method is also provided using the device.

16 Claims, 1 Drawing Sheet

OTHER PUBLICATIONS

"Spinel." (1992). In Academic Press Dictionary of Science and Technology, Oxford: Elsevier Science & Technology.

International Search Report dated Jun. 14, 2006 concerning International Appl, No. PCT/EP2006/001765.

German Office Action dated Nov. 16, 2005 for German Appl. No. 10200501181.552.

Office Action dated Aug. 24, 2010 form the Australian Patent Office in counterpart Australian Application No. 2008202464.

* cited by examiner

DEVICE FOR COLLECTING GASES IN MOLTEN METAL AND MEASUREMENT METHOD

BACKGROUND OF THE INVENTION

The invention relates to a device for collecting gases in molten metals, the device comprising an immersion end having a collection body, a gas supply line opening at the immersion end, and a gas discharge line for the gases penetrating the collection body, wherein the gas collection body has an end face arranged on the immersion end and side walls. In addition, the invention relates to a method for measuring a gas content in a molten metal, wherein gas is introduced into the molten metal, there enters into a gas exchange with gas contained in the molten metal, and then is taken up and fed to a measurement device for evaluation. At least two different gases are introduced into the molten metal and evaluated, both gases having a respective carrier gas and optionally an admixture of a gas, whose percentage in the molten metal is to be determined.

Such devices are known, for example, from German published patent application DE 10 2005 011 181 A1 or from European Patent EP 307 430 B1. In such devices, gases from a molten metal are collected and fed to a measurement device, so that the contents of certain gases contained in the molten metal can be measured. For this purpose, a gas supply line for feeding reference gas or carrier gas into the molten metal is led through the gas collection body and out of the body at its end face. With the help of the gas supply line, reference gas is blown into the molten metal. The reference gas becomes enriched with the gases in the molten metal or, according to another procedure, the reference gas has a higher concentration of the gas to be measured than the molten metal, so that the resulting gas mixture has a smaller concentration of the gas component to be measured than the reference gas. The resulting gas mixture is taken up by the gas collection body, fed through the gas discharge line to the measurement device, and evaluated. The measurement method is described in detail, for example, in European Patent EP 307 430 B1. Such measurement methods are also described in European patent application publication EP 563 447 A1.

Similar devices are known from U.S. Pat. No. 6,216,526 B1 and from European patent application publication EP 295 798 A1.

BRIEF SUMMARY OF THE INVENTION

An object of the present invention is to improve the known gas collection devices and to increase the efficiency of the collection process and also the measurement method.

The object is achieved by a device for collection of gases in molten metals, the device comprising an immersion end having a gas collection body, a gas supply line opening at the immersion end, and a gas discharge line for the gases penetrating the gas collection body, wherein the gas collection body has an end face arranged on the immersion end and side walls, and wherein at least a portion of the gas collection body has a gas impermeable layer.

Due to at least one part of the gas collection body having a gas impermeable layer, it is thus possible to capture a larger portion of the gases by the gas collection body and to feed this portion to the gas discharge line and thus to the measurement device. Thus, the gases penetrating into the gas collection body, at least essentially, can no longer leave the gas collection body except from the gas discharge line, so that a significantly larger portion of the gases taken up in the gas collection body can be fed to the measurement device. In this way, the measurement is simpler, quicker, and finally also more precise.

It is expedient that at least one part of the outer side walls of the collection body have a gas impermeable layer. The gas collection body itself can have on its end face a hollow space, already known from the prior art (see above). The gases coming out of the melt initially collect in this hollow space. They then penetrate into the gas collection body, because they cannot escape any other way from the hollow space. Due to the side shielding by the gas impermeable layer, the gases can escape only into the gas discharge line. For this purpose, the gas impermeable layer can be arranged on the surface of the side walls of the gas collection body.

It is advantageous that the impermeable layer be formed of at least two sub-layers arranged one on top of the other. The lower sub-layer facing the interior of the gas collection body can be made of metal, in particular of a metal with a higher melting point than iron. The metals can be, in particular molybdenum, titanium, vanadium, chromium, niobium, or an alloy with at least one of these metals. The lower, inner sub-layer is gas-tight. An outer sub-layer facing away from the interior of the gas collection body and made of ceramic can be applied on this inner sub-layer. This outer sub-layer can act as a protective layer for the lower sub-layer made of metal, arranged between it and the gas collection body. The outer sub-layer can be formed preferably from oxide ceramic or a silicate, in particular from zirconium dioxide, aluminum oxide, chromium dioxide, zirconium silicate, aluminum silicate, or spinel.

The gas collection body can be almost completely surrounded with the layer, wherein only the end-face gas inlet into the gas collection body and the entrance to the gas discharge line from the gas collection body are not coated. It is sensible to leave the entire end face of the gas collection body uncoated or even only the surface of the end-face hollow space of the gas collection body. Preferably, at least one of the sub-layers is applied by plasma spraying.

Expediently, the gas collection body can have a cylindrical or conical side wall. The gas discharge line is preferably arranged on the back wall of the gas collection body lying opposite the end face. The gas discharge line can be arranged, for example, on a gas supply connector or in an opening of the gas collection body.

The device is used according to the invention for measuring the gas content in a molten metal. Measurements are possible, for example, in a wide variety of different molten metals. The gas collection body itself is impermeable to the molten metal, but exhibits very good gas permeability and receptivity for the gases to be measured.

The object is further achieved by a method for measuring a gas content in a molten metal, wherein gas is introduced into the molten metal, there enters into a gas exchange with gas contained in the molten metal, and then is taken up and fed to a measurement device for evaluation. At least two different gases are introduced into the molten metal and evaluated, both gases having a respective carrier gas and optionally an admixture of one gas, whose percentage in the molten metal is to be determined.

According to the invention, the measurement method is characterized in that, in each case of gas introduction, the concentration of the admixed gas lies either below or above the concentration of the gas to be measured in the molten metal. Here, the method starts with the assumed gas concentration in the molten metal, and a concentration either significantly below or significantly above the expected concentration in the molten metal is selected for the gas to be introduced. Then, for the two gases, the gas to be measured is either absorbed or desorbed in the molten metal. Thus, the measurement is performed with two (or more) gases, which are independent of each other. Here, the same or different carrier gases can be used. The gases introduced into the melt absorb gas from the melt if the concentration of the gas to be determined in the molten metal is higher than the concentration of this gas in the introduced gas, so that, as the introduced gas, a pure carrier gas can also be used and the concentration of the gas to be measured can be zero in the introduced gas. In the opposite case, the molten metal absorbs gas from the introduced gas, because in each case the goal is naturally equilibrium. For the measurement, the circumstance can be used that the absorption and the desorption characteristics of different gases in molten metals can be different.

As the carrier gas, inert gases can be used, preferably argon and/or nitrogen. As the admixed gas, carbon monoxide can be used, so that the carbon monoxide content in the molten metal can be measured.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

The sole drawing FIGURE is a schematic, longitudinal, partially sectioned view of a device according to one embodiment of the invention.

DETAILED DESCRIPTION OF THE INVENTION

Figure 1:
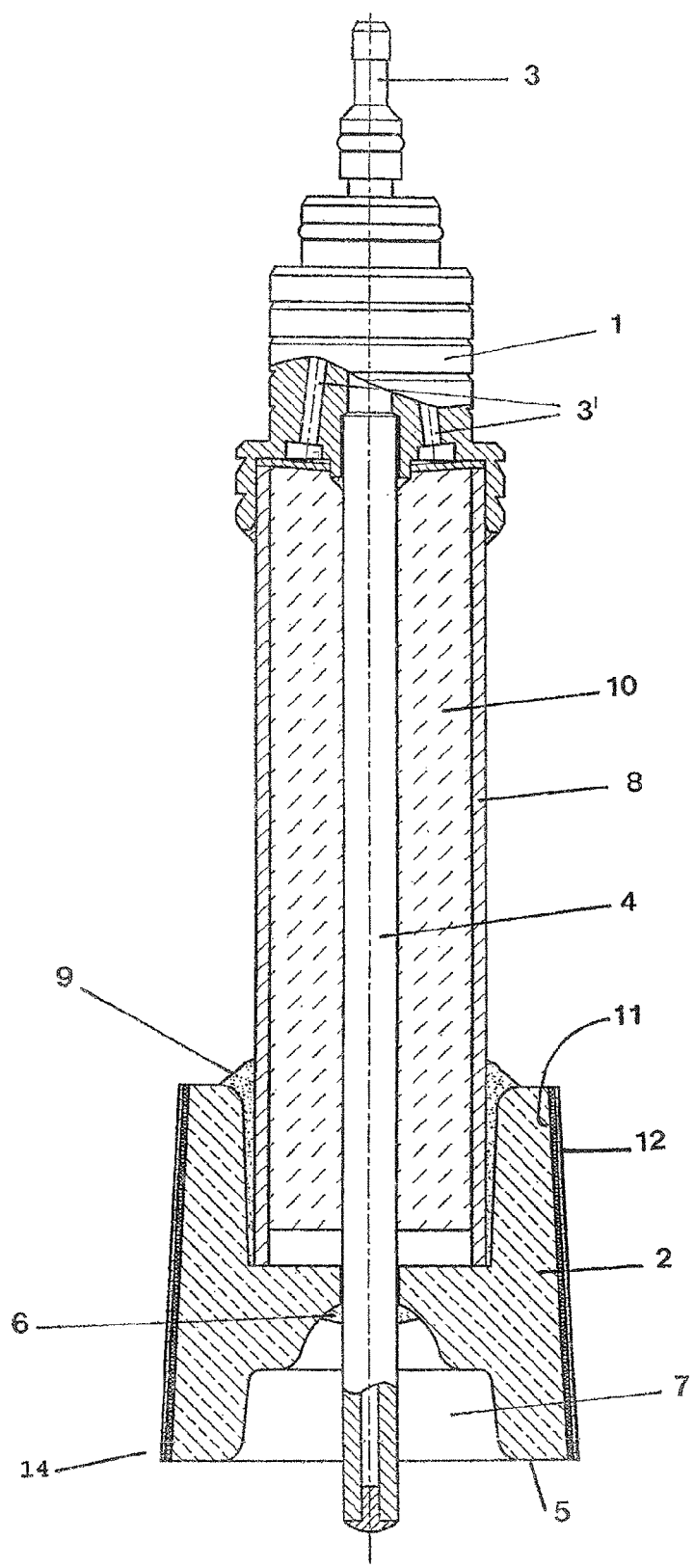

The device shown in the drawing is fixed to an attachment nozzle 1 on a carrier tube (not-shown) and is immersed with this tube into a molten metal. The gas collection body 2 is immersed into the molten metal, in order to perform the gas exchange.

In the attachment nozzle 1 there are gas connections 3; 3'. Here, the central gas connection 3 opens into the gas supply line 4 arranged centrally in the device. This supply line is guided centrally through the gas collection body and ends beneath the end face 5 of the gas collection body. Carrier gas is introduced into the molten metal through the gas supply line 4. The gas supply line 4 is made essentially of a quartz tube, which can be bent on its immersion end, so that the opening is oriented in the direction of the gas collection body 2. The gas supply line 4 is fixed in the gas collection body 2 by means of cement 6.

The carrier gas flowing into the molten metal through the gas supply line 4 absorbs gases from the molten metal, rises into the hollow space 7 of the gas collection body 2, and penetrates from there and from the end face 5 into the gas collection body 2. This is formed of a porous material, for example of cement. A ceramic body, for example aluminum oxide, is also possible. The gas penetrates upward into the gas discharge line through the pores of the gas collection body. This discharge line is formed essentially of a quartz glass tube 8, which is fixed in the gas collection body 2 by cement 9.

In the quartz glass tube there is a porous filling 10 made of aluminum oxide, for example in a spherical shape. Through the filling 10 the carrier gas mixed with gas from the molten metal is discharged through the gas connections 3' to a measurement device. There, the extracted gas is compared with the gas introduced into the molten metal, and thus the gas absorbed (or desorbed) from (or to) the melt is evaluated, and the gas content in the molten metal is determined thereby.

This process is sufficiently well known per se and described, for example in European Patent EP 307 430 B1 (or similarly in European patent application publication EP 563 447 A1). Argon is used as the carrier gas of the introduced gas. Carbon monoxide at a percentage of more than 2.5% (for example 5% or 10%) is admixed with the carrier gas for measuring the carbon monoxide content in the molten steel, since the expected gas content lies at 2.5%.

The gas collection body 2 has on its conical outer surface a gas impermeable layer made of a lower sub-layer 11 and an outer sub-layer 12. The lower sub-layer 11 is formed of molybdenum. The outer sub-layer 12 is used as a protective layer and is made of spinel.

In principle, the gas impermeable layer can also be arranged on the end of the gas collection body 2 facing the immersion end 14. However, in the normal case this is not necessary, because the surfaces provided there are small, so that gas leakage occurs only to an insignificant extent. Therefore, in practice all of the gas taken up by the device is fed into the gas discharge line defined by the quartz glass tube 8.

With the device, the content of hydrogen or nitrogen in molten steel can also be determined.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for collection of gases in molten metals, the device comprising an immersion end having a gas collection body, a gas supply line opening at the immersion end, and a gas discharge line for gases penetrating the gas collection body, wherein the gas collection body has side walls and an end face arranged at the immersion end, and wherein at least a portion of the gas collection body has a gas impermeable layer which is arranged on a surface of the side walls of the gas collection body and which comprises at least two sub-layers arranged one on top of the other, a lower sub-layer facing an interior of the gas collection body and comprising a metal.

2. The device according to Claim 1 wherein the lower sub-layer comprises a metal with a higher melting point than iron.

3. The device according to Claim 1, wherein the lower sub-layer is formed essentially of a metal selected from molybdenum, titanium, vanadium, chromium, niobium, and an alloy with at least one of these metals.

4. The device according to Claim 1, wherein an outer sub-layer facing away from an interior of the gas collection body comprises ceramic.

5. The device according to claim 4, wherein the outer sub-layer comprises an oxide ceramic or a silicate.

6. The device according to claim 5, wherein the outer sub-layer is formed of a metal compound selected from zirconium dioxide, aluminum oxide, chromium dioxide, zirconium silicate, aluminum silicate, or spinel.

7. The device according to claim 1, wherein the gas collection body has a cylindrical or conical side wall.

8. The device according to claim 1, wherein the gas discharge line is arranged on a back wall of the gas collection body lying opposite the end face.

9. The device according to claim 1, wherein the gas discharge line is arranged on a gas connection nozzle or in an opening of the gas collection body.

10. A method for measuring a gas content in a molten metal, comprising the steps of:
    introducing at least two different gases into the molten metal, the introduced gases entering into a gas exchange with a gas contained in the molten metal; and
    taking up and feeding the exchanged gases to a measurement device for evaluation, and
    evaluating the exchanged gases to determine the gas content,
    wherein each of the at least two introduced gases includes a carrier gas and a gas admixed with the carrier gas, the admixed gas being the same as the gas contained in the molten metal whose content is to be measured, and
    wherein for both of the introduced gases, the concentration of the admixed gas is either below or above the concentration of the gas contained in the molten metal whose content is to be measured.

11. The method according to claim 10, wherein the introduced gases have different carrier gases.

12. The method according to claim 10, wherein an inert gas is used as the carrier gas.

13. The method according to claim 12, wherein the inert gas is selected from argon and nitrogen.

14. The method according to claim 10, wherein the admixed gas is carbon monoxide.

15. The method according to claim 10, wherein the concentration of the admixed gas is zero in case of a lower concentration than the concentration of the gas to be measured.

16. A device for collection of gases in molten metals, the device comprising an immersion end having a gas collection body, a gas supply line opening at the immersion end, and a gas discharge line for gases penetrating the gas collection body,
    wherein the gas collection body has side walls and an end face arranged at the immersion end, and
    wherein at least a portion of the gas collection body has a gas impermeable layer which is arranged on a surface of the side walls of the gas collection body and which comprises at least two sub-layers arranged one on top of the other, at least one of the sub-layers being applied by plasma spraying.

* * * * *